Figure 1:
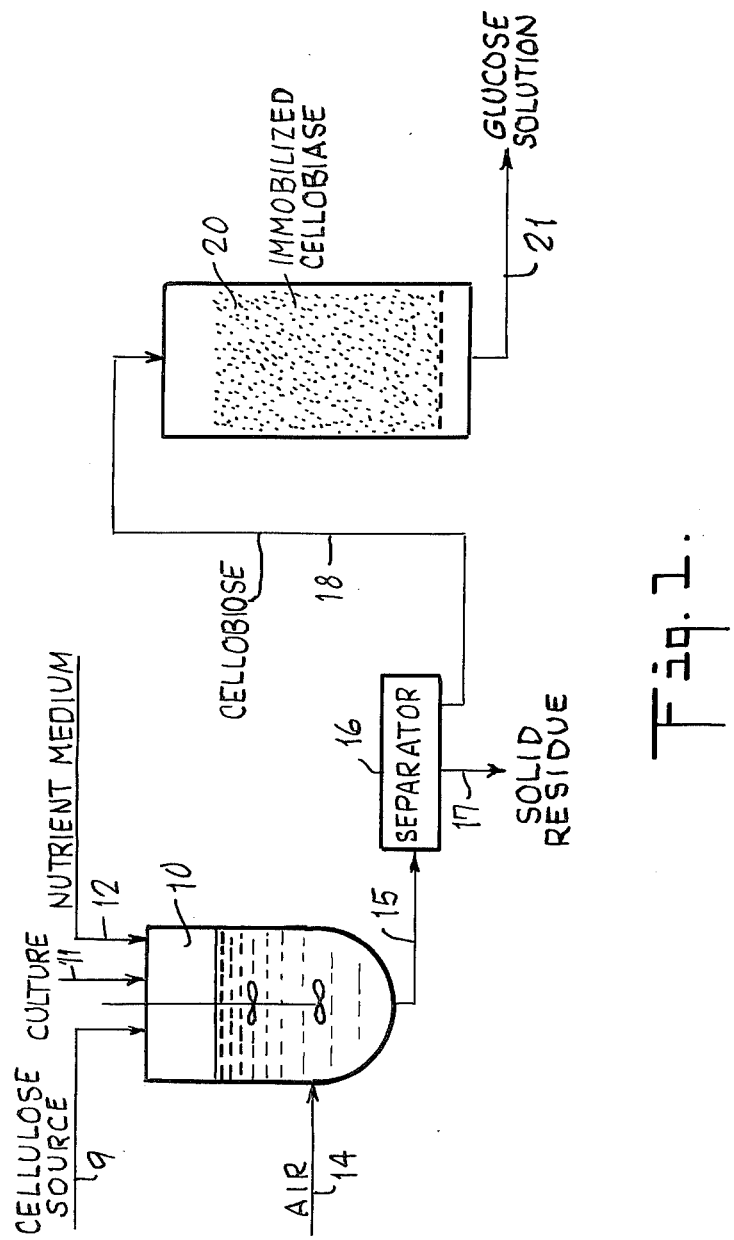

United States Patent [19]
Day et al.

[11] Patent Number: 4,487,831
[45] Date of Patent: Dec. 11, 1984

[54] PROCESS FOR THE CONVERSION OF CELLULOSE TO GLUCOSE

[75] Inventors: Donal F. Day; Wesley E. Workman, both of Baton Rouge, La.

[73] Assignee: Research Corporation, New York, N.Y.

[21] Appl. No.: 380,025

[22] Filed: May 19, 1982

[51] Int. Cl.³ .............. C12P 19/14; C12N 9/42; C12R 1/66; C12R 1/885
[52] U.S. Cl. .................. 435/99; 435/209; 435/815; 435/913; 435/945
[58] Field of Search ............ 435/209, 99, 162, 163, 435/815, 913, 200

[56] References Cited
PUBLICATIONS

Chemical Abstracts vol. 79, 50164h (1979).
Chemical Abstracts vol. 96, 4906e (1982).
Hajny et al., Cellulases and Their Applications (1969) pp. 37 to 42.
Reese, Enzymatic Hydrolysis of Cellulose and Related Materials 1963 pp. 106–114.
Tsao, editor, Annual Reports on Fermentation Processes, vol. 5 (1982) Chapter 2 Cellulases, pp. 50–58.
American Type Culture Collection Catalog of Strains 15th Ed. 1982, p. 294.

Primary Examiner—Lionel M. Shapiro
Attorney, Agent, or Firm—Scully, Scott, Murphy & Presser

[57] ABSTRACT

Cellulose is converted to glucose in a two stage process in which cellobiose is produced from a cellulosic feedstock under the influence of *Trichoderma reesei* in a first stage and cellobiose from the first stage is converted to glucose in a second stage by the action of purified cellobiase derived from *Aspergillus terreus*. Cellobiase from *A. terreus* is purified by contacting a crude aqueous extract of the cellobiase with an ion exchange resin and an anion exchange resin. The purified cellobiase may be immobilized on a suitable substrate.

19 Claims, 2 Drawing Figures

PROCESS FOR THE CONVERSION OF CELLULOSE TO GLUCOSE

The present invention relates to a process for the production of glucose from cellulose. In one of its more specific aspects, this invention relates to a process for the conversion of cellulose to glucose wherein cellulose is converted to cellobiose under the influence of *Trichoderma reesei* and cellobiose is converted to glucose by a purified cellobiase derived from *Aspergillus terreus*. In another of its more specific aspects, this invention relates to a process for the production of a purified enzyme having a very high activity for the production of glucose from cellobiose.

There is presently tremendous scientific and commercial activity in the quest for economic means to convert cellulose (abundant in the form of wood, waste paper, and agricultural products, e.g. bagasse) to glucose and thence to ethanol and other chemicals. Cellulose may be converted to glucose by the action of various enzymes derived from molds.

It is known from the prior art that *Trichoderma reesei* is a fungus that has the ability to degrade cellulose very rapidly. Currently *Trichoderma reesei* is the preferred orgnaism for studies in the hydrolysis of cellulose to glucose for industrial purposes. The conversion of cellulose to glucose is not yet economically feasible, due partially to the fact that the cellobiase produced by *Trichoderma reesei* has a low specific activity. Additionally, glucose, which is the final product of reaction, further inhibits the activity of the *Trichoderma reesei* enzymes.

We have discovered an efficient method for the conversion of cellulose to glucose in a two stage process. In the first stage, cellulose is converted to cellobiose by the action of a cellulase produced by *Trichoderma reesei*, and in the second stage, cellobiose is converted to glucose by the action of a purified cellobiase produced by *Aspergillus terreus*. This is a distinct departure from the prior art processes in which *Trichoderma reesei* enzymes perform both functions at efficiencies and conversion rates considerably less than those obtained in our process.

We have also discovered a novel ion exchange method for the purification of a cellobiase from a water extract of a biomass comprising a cellobiase-producing mold. The method of our invention has been successfully applied to the production of a purified cellobiase from *Aspergillus terreus* which rapidly and efficiently converts cellobiose to glucose. Our ion exchange method of purification of enzymes is not limited to purification of the cellobiase from *Aspergillus terreus* but also may be applied to purification of other glycoproteins having a large neutral carbohydrate portion, for example, inulinase from the yeast *Kluveromyces fragilis*. We believe that the effectiveness of our purification method for enhancing the effectiveness of cellobiase from *Aspergillus terreus* is due in part to the unique properties of this particular enzyme.

U.S. Pat. No. 3,269,918 discloses a process for purifying glucose oxidase with an anionic ion exchange material. U.S. Pat. No. 3,658,651 discloses a process for purifying bromelain-containing juice extracted from pineapple plant stems by contacting the juice with anionic and cationic exchange resins prior to precipitation of the enzyme. Ion exchange resins have been used heretofore to a limited extent for the purification of enzymes, but we are not aware of any prior art relating to purification of cellobiase by the method disclosed herein.

The fungus cultures which are employed in the process of this invention may be prepared and maintained by conventional biological procedures well known in the art. Although a single fungus species is preferred for production of each of the enzymes employed in the two stages of our process, the preferred fungus may be mixed with others. Usually the fungi useful in the process of this invention are mixed in their natural environments with other cellulase or cellobiase producing fungi. Such mixtures may be used in the present process so long as the preferred species is predominant and the coexisting fungi do not appreciably depress the yields of the desired enzymes.

An organic carbon nutrient source serves to support the metabolism of the fungi. The growth of the desired fungus is enhanced by the presence of various carbohydrates, e.g., sucrose, lactose, maltose, glucose, succinates, formates, citrates, cellulose, hemi-cellulose, and cellobiose, among other organic compounds. The nutrient medium is preferably acidic with a preferred pH range of 5 to 6 maintained with a suitable buffer, for example, potassium phosphate or sodium phosphate.

Separation of the biomass from the broth or aqueous nutrient medium in which it is cultivated may be carried out by conventional methods, for example, by filtration or centrifugation. Centrifugal separation is generally preferred since filtration media are clogged to varying degrees by the fungal cells. The aqueous nutrient may be reused for the fermentation of additional fungus.

The recovered fungal cells are resuspended in a buffer solution and subjected to cell fracturing, suitably by acid treatment, vigorous agitation, or sonic vibration, after which the fungal mass is separated from the aqueous medium comprising enzymes produced by a fungus. Tween ® 80, a surface-active agent consisting of partial esters of long-chain fatty acids with polyoxyalkylene derivatives of hexitol anhydride is a useful wetting agent for dispersion of the fungal cells and recovery of enzymes from the fungal mass.

Figure 2:
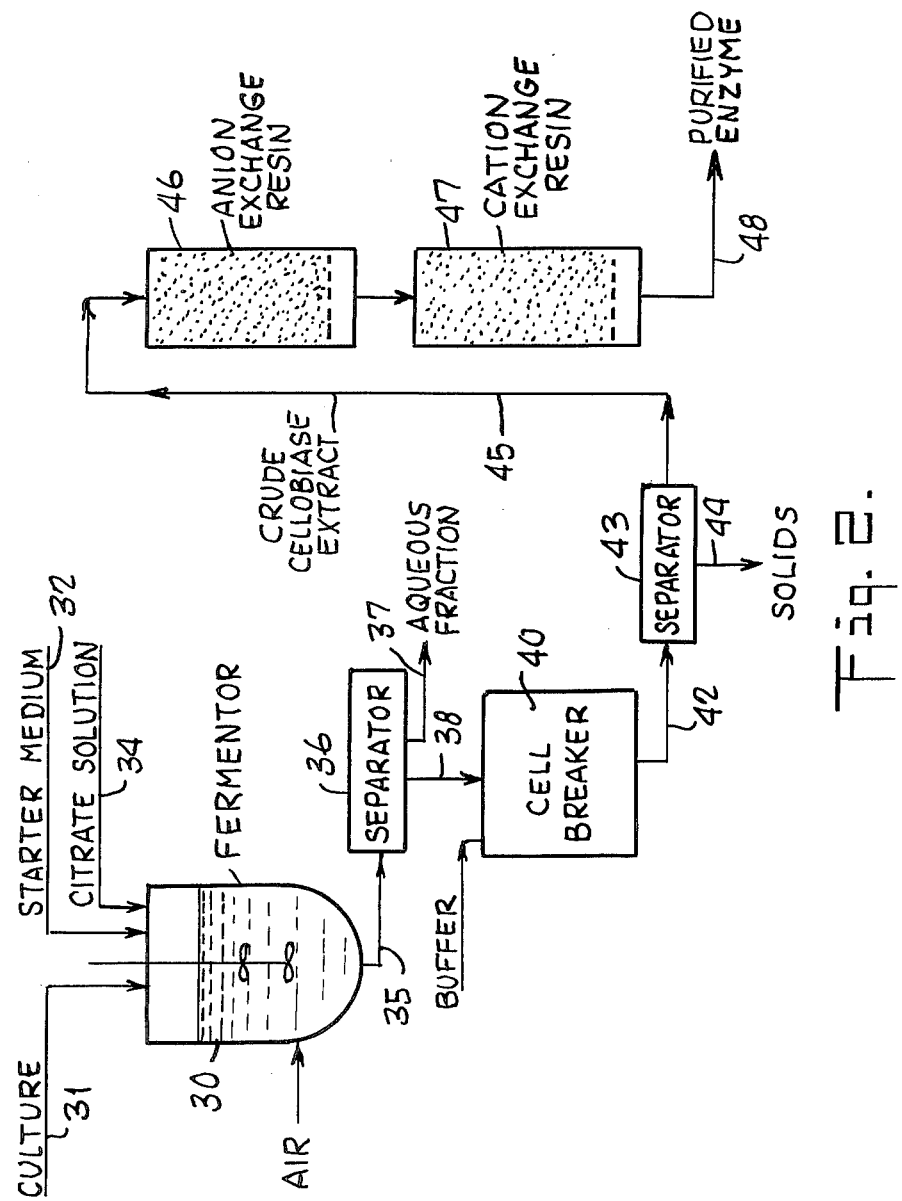

The process of the present invention may be more readily understood with reference to the accompanying drawings in which FIG. 1 is a diagrammatic flow sheet illustrating one embodiment of the method of this invention for the conversion of cellulose to glucose and FIG. 2 is a diagrammatic flow sheet illustrating the method of extracting and purifying an enzyme in accordance with the method of this invention.

With reference to FIG. 1 of the drawings, culture in the form of mold or mold spores is introduced into a fermentor 10 suitably a vessel provided with a stirrer, from line 11 together with culture medium supplied from line 12. The culture may be premixed with or suspended in the culture medium prior to introduction into fermentor 10. The culture is maintained at a temperature in the range of 25° to 30° C., preferably at about 28° C., with gentle aeration and vigorous agitation to promote growth of the organism. A preferred culture for the conversion of cellulose into cellobiose is *Trichoderma reesei*. Air may be introduced into the fermentor tank 10 through line 14 as required. At the end of the fermentation period, a cellulosic feedstock, preferably a partially purified cellulose in finely divided form, is introduced into the fermentor 10 through line 9 and the temperature increased to the range of 47° to 53°

C., preferably about 50° C. effecting conversion of cellulose to cellobiose.

Biomass containing the fungus *Trichoderma reesei* is withdrawn continuously or intermittently from fermentor 10 through line 15 to a separator 16, preferably a centrifuge. Solids comprising the fungal biomass and unconverted portions of the cellulose source are separated from the aqueous solution containing cellobiose. Solids discharged from separator 16 through line 17 may be subjected to further extraction for recovery of cellobiose by resuspending the solid residue in a buffered aqueous medium and repeating the separation step. The aqueous solution separated from the biomass in separator 16 is passed through line 18 to converter 20 where it is contacted with a bed of immobilized cellobiase on a suitable carrier material converting cellobiose to glucose. The aqueous solution discharged from converter column 20 through line 21 may be further processed for conversion of glucose to alcohols by known processes not illustrated in the figure.

In general, the fermentation process carried out in fermentor 10 is an aerobic process. Suitable growth media comprise a carbon source, a nitrogen source, oxygen, and trace mineral elements necessary for the growth of the mold.

The preferred cellobiase contained in converter 20 is a purified cellobiase from *Aspergillus terreus* produced in accordance with the method of this invention and immobilized on a suitable carrier. Methods for the immobilization of the cellobiase enzyme are disclosed in Japanese patent application Nos. 76/108,154 and 76/108,155, filed Sept. 9, 1976, and published Mar. 31, 1978. We have successfully immobilized the *A. terreus* enzyme on chitin and glass with glutaraldehyde by known procedures. Maximum enzyme attachment is achieved at an activity to weight ratio (purified enzyme to support) of 10:1000. Very little inactivation of the purified enzyme occurs on immobilization.

With reference to FIG. 2, illustrating a preferred method for the preparation of the purified enzyme cellobiase, the mold culture or spores is introduced into a fermentor vessel 30 from line 31 and culture medium is supplied from line 32. Air is introduced into the fermentor through line 33. The Czapek-Dox culture medium, described in U.S. Department of Agriculture Bureau of Animal Industry Bulletin, 120:70 (1910), incorporated herein by reference, is suitable for the production of *Aspergillus terreus* from which the active cellobiase enzyme is extracted and purified in accordance with the present invention. The Czapek-Dox medium is a synthetic culture medium in which nitrate is the sole source of nitrogen. Temperatures in the range of 25° to 40° C. are optimum for the growth of molds which yield cellobiase.

A satisfactory medium may be prepared by making up an aqueous solution containing the components and the concentration ranges for each as shown in Table 1.

TABLE 1

| Starter Medium | |
|---|---|
| Component | Molar Concentration |
| Sodium Nitrate | $3.5 \times 10^{-2}$ |
| Potassium Chloride | $6.7 \times 10^{-3}$ |
| Dipotassium Phosphate | $5.7 \times 10^{-3}$ |
| Magnesium Sulfate | $2.0 \times 10^{-3}$ |
| Ferrous Sulfate | $4.0 \times 10^{-5}$ |

TABLE 1-continued

| Starter Medium | |
|---|---|
| Component | Molar Concentration |
| Glucose | 0.028 |

In a preferred embodiment of the present invention, the culture, suitably as an aqueous suspension, is added to the starter medium and introduced into fermentor 30 where it is maintained at 35° C. with gentle aeration at a rate of 0.2 to 0.25 liters of air per liter of nutrient solution per minute and vigorous agitation, e.g. 3600 rpm with a mechanical stirrer, for two days. After two days of incubation in the starter medium, a citrate medium is fed into the fermenter. A concentrated citrate medium is made up and fed to the fermentor with water to produce a gradient starting with plain water and ending with 0.14 molar potassium citrate. A suitable concentrated citrate medium is shown in Table 2.

TABLE 2

| Concentrated Citrate Medium | |
|---|---|
| Component | Molar Concentration |
| Sodium Nitrate | $7.0 \times 10^{-2}$ |
| Potassium Chloride | $1.3 \times 10^{-2}$ |
| Dipotassium Phosphate | $1.1 \times 10^{-2}$ |
| Magnesium Sulfate | $4.0 \times 10^{-3}$ |
| Ferrous Sulfate | $4.3 \times 10^{-4}$ |
| Potassium Citrate | 0.14 |

The concentrated citrate medium is adjusted to a pH within the range of 3.5 to 6, preferably 4.5. A gradient of the citrate medium is fed into the fermentor 30 through line 34 at a feed rate of 1 to 1.1 milliliters per liter of starter medium per minute for a period of two days. During the addition of the citrate medium to the fermentor, a gradient is maintained by gradually blending the concentrated citrate medium with water in a linear manner starting with 100 percent water by volume and ending with 100 percent concentrated citrate medium by volume. A total of three liters of citrate gradient per liter of starting medium is added to the fermentor over the two day period while temperature, aeration rate, and agitation remains substantially constant.

Cellulose or carboxymethylcellulose may be substituted for the citrate medium, but is more difficult to handle than the citrate.

At the end of the fermentation period, which may range in practice from two to four days, biomass containing the fungus *Aspergillus terreus* is withdrawn from fermentor 30 through line 35 to separator 36 wherein the aqueous medium is separated from the biomass solids, preferably by a centrifuge. The aqueous fraction is discharged from separator 36 through line 37. The aqueous fraction may be reused in the fermentation of additional biomass or discarded. The biomass solids, consisting essentially of the mold cells, is discharged through line 38 into a vessel 40 to which buffer is added through line 41. A 0.05M potassium phosphate buffer (pH 6.0) is suitable for this purpose. In the vessel 40 the cells are ruptured by acid treatment, vigorous stirring or sonic vibration from a suitable source. Methods of rupturing the cells are well known in the art.

A suspension of mold cells and debris is withdrawn from vessel 40 through line 42 to separator 43, suitably a centrifuge, wherein the cells and solid debris are separated from an aqueous solution comprising cellobiase.

Solids separated from the crude cellobiase extract in separator 43 are discharged through line 44 and may be further processed for the recovery of cellobiase by re-extraction in one or more additional extraction stages, not illustrated.

The crude cellobiase extract from separator 43 passes through line 45 to a purification process which comprises extraction of protein from cellobiase by ion exchange resins. In the process of our invention, the crude cellobiase extract is contacted at pH6 with an anion exchange resin and a cation exchange resin, either sequentially or simultaneously. Insofar as the purification process is concerned, the crude cellobiase extract may be first contacted with the anion exchange resin followed by contact with the cation exchange resin, or vice-versa, or with a mixture of anion and cation exchange resins. As illustrated in the figure, crude cellobiase extract from line 45 is contacted with a bed of anion exchange resin in vessel 46 and then contacted with a bed of cation exchange resin in vessel 47.

By way of example, but not by way of limitation, we have found that an anion exchange resin containing diethylaminoethyl groups and a cation exchange resin containing carboxymethyl groups is effective for removal of a major portion, usually of the order of 62 percent, of the contaminating protein from the cellobiase with complete recovery of the enzyme when applied to the crude cellobiase extract derived from *A. terreus*. This purification process has the advantage of being a continuous process until such time as the amount of contaminating protein bound to the ion exchange resin exceeds the capacity of the resin. At that time, the resin can be regenerated while still in the column by flushing with dilute acid and base solutions and adjustment of the pH before reuse.

Purified enzyme is discharged from the purification system through line 48. The purified enzyme has an extremely high activity for the conversion of cellobiose to glucose and is preferred as the cellobiase employed in converter 20 of FIG. 1.

The following example describes in detail a preferred embodiment of the present invention.

EXAMPLE

*Aspergillus terreus* (ATCC 20514) stock cultures were maintained at room temperature on potato dextrose agar (Difco) plates. A culture media was prepared which consisted of $3.5 \times 10^{-2}$M sodium nitrate, $6.7 \times 10^{-3}$M potassium chloride, $5.7 \times 10^{-3}$M dipotassium phosphate, $2.0 \times 10^{-3}$M magnesium sulfate, $4.0 \times 10^{-5}$M ferrous sulfate, and 0.028M glucose in four liters of distilled water.

The resulting media preparation containing 0.028M glucose (pH 7.3) were added to a 16 liter fermentor vessel. The spores from one potato dextrose agar plate were harvested by adding 25 ml of a 2% by volume Tween®80 solution to the plate and suspending the spores by scraping the plate. The spore suspension was then transferred to the fermentation vessel. The culture was maintained at 35° C. with gentle aeration (0.9 liter/minute) and vigorous agitation (3600 rpm) with an overhead stirrer. After two days of incubation, a citrate medium was introduced into the mycelial inoculum.

Concentrated citrate medium was prepared containing $7.0 \times 10^{-2}$M sodium nitrate, $1.3 \times 10^{-2}$M potassium chloride, $1.1 \times 10^{-2}$M dipotassium phosphate, $4.0 \times 10^{-3}$M magnesium sulfate, $4.3 \times 10^{-4}$M ferrous sulfate and 0.14M potassium citrate in 6 liters distilled water and was adjusted to pH 4.5. A gradient of the citrate medium and water was fed into the fermentor starting with 0.0M potassium citrate and ending at 0.14M. The rate of feed was 4.2 ml/min. Citrate medium was fed into the fermentor in such a manner that the concentration pumped into the fermentor increased linearly from 0.0M citrate to 0.14M citrate over a period of two days. A gradient maker of 12 liter capacity which mixed linearly 6 liters of the concentrated citrate medium with 6 liters of sterile water was used to produce the gradient. The nutrient gradient was fed at a flow rate of 4.2 ml/minute for two days. Temperature, aeration, and agitation remained constant. All media and equipment used for culturing the organism were sterilized prior to incubation and the culture was periodically checked for contamination. After the gradient was complete, the cells were harvested by filtration on Whatman No. 1 paper and then resuspended in 400 ml of 0.05M potassium phosphate buffer (pH 6.0).

100 ml of the resulting cell slurry biomass was combined with 100 ml of 0.05M potassium phosphate buffer (pH 6.0). The beaker containing the cell suspension was placed in an ice bath and the cells broken by sonication. The suspension was then centrifuged at 13,000 g for 10 minutes. The packed cells and debris were resuspended in three volumes of 0.05M potassium phosphate buffer (pH 6.0), sonicated and centrifuged as described previously. The procedure was repeated for a third time. The supernates from each centrifugation were combined and filtered through glass wool. This fraction is referred to as the crude enzyme.

The β-glucosidase activity was routinely determined using p-nitrophenyl-β-D-glucoside (PNPG) as the substrate. Two milliliters of a 10 mM PNPG solution in 0.05M sodium citrate buffer solution (pH 4.8) were heated to 50° C. Then 251 of the enzyme solution was added to the substrate and incubated for 15 minutes. After incubation, 3 ml of 1.0M aqueous sodium carbonate solution were added to stop the reaction and develop the color. The absorbance was read at 400 nm and the amount of p-nitrophenol liberated was determined from a standard curve. The time of incubation varied depending on the activity of the enzyme preparation tested. A unit (IU) of activity was defined as the amount of enzyme required to liberate one micromole of p-nitrophenol per minute from the substrate.

The activity on cellobiose was determined by two different methods. In the first method 0.4 ml of the substrate, 12.5 mM cellobiose in 0.0625M sodium citrate buffer (pH 4.8), was preheated to 50° C., then 0.1 ml of the preheated enzyme solution was added to the substrate and the tubes stoppered. Each sample was incubated for 1.5 minutes placed in a boiling water bath for 30 seconds and then immediately cooled in an ice bath. This reaction mixture was added to 5 ml of the glucose oxidase reagent from a glucose assay kit (Sigma Chemical Co.) and the amount of glucose produced from cellobiose hydrolysis was determined spectrophometrically.

In the second method the amount of glucose produced was measured on a high pressure liquid chromatograph. The cellobiose substrate consisted of 0.03M cellobiose in 0.075M sodium citrate buffer (pH 4.8). The substrate and enzyme solution was preheated to 50° C., then 0.25 ml of the enzyme solution was added to 0.5 ml of the substrate and incubated for 10 minutes. After the incubation, the sample was heated in boiling water for 30 seconds and then cooled in crushed ice. A 20 ml aliquot was assayed for glucose by high pressure liquid chromatography.

Using cellobiose as the substrate, the purified cellobiase enzyme from *Aspergillus terreus* was capable of producing 215 micromoles of glucose from cellobiose per minute per milligram of enzyme protein. A unit of cellobiase activity was defined as the amount of enzyme that produced one micromole of glucose per minute from cellobiose. The specific activity of our purified cellobiase is expressed as 215 units per mg protein. This enzyme also has an affinity ($K_m$) of $4.0 \times 10^{-4}$M for cellobiose. $K_m$ is a term equal to the concentration of substrate (cellobiose) that enables the enzyme to perform at one-half its maximum velocity, therefore, the smaller the $K_m$ the greater the affinity for the substrate. Included in Table 3 are all the specific activities and $K_m$ values of purified cellobiase from *A. terreus* as compared ith *Aspergillus phoenicis* and *Trichoderma reesei* as reported in the literature.

TABLE 3

| Organism | Specific Activity[1] units/mg Protein | $K_m$[2] molar |
|---|---|---|
| Aspergillus terreus | 215 | $4.0 \times 10^{-4}$ |
| Aspergillus phoenicis | 160 | $7.5 \times 10^{-4}$ |
| Trichoderma reesei | 0.89 | $3.3 \times 10^{-3}$ |

[1] Specific activity refers to the rate at which the enzyme works. A unit of activity is defined as the micromoles of glucose produced from cellobiose per minute. Therefore, the larger the specific activity the faster the enzyme works.
[2] Km refers to the affinity and is called the Michaelis-Menten constant. The smaller the Km the greater is the affinity between the enzyme and the substrate.

Glucose is a competitive inhibitor of the cellobiase enzyme from *Aspergillus terreus*. When p-nitrophenyl-β-D-glucoside was used as the substrate, a $K_i$ dissociation constant of $3.5 \times 10^{-3}$M was obtained for glucose. The $K_i$ is the concentration of inhibitor required to slow the reaction down to one-half its maximum velocity, therefore, the larger the $K_i$ the less inhibitory the inhibitor is. Our purified cellobiase is inhibited to a lesser extent than any of the other reported cellobiases as indicated in Table 4.

TABLE 4

| Cellobiase source | Type of Inhibition | Ki (molar) | Reference |
|---|---|---|---|
| Aspergillus terreus | competitive | $3.5 \times 10^{-3}$ | — |
| Alcaligenes faecalis | competitive | $3.0 \times 10^{-3}$ | (1) |
| Lenzites trabes | noncompetitive | $2.7 \times 10^{-3}$ | (2) |
| Phanerochaete chrysosporium | competitive | $5.0 \times 10^{-4}$ | (3) |

(1) Ivanova, I., etal (1980). Prikl. Biokhim. Microbiol. 16:60-64
(2) Herr, D. etal (1978). Eur. J. Microbiol. Biotechnol. 5:29-36
(3) Smith M. and M. Gold (1979) Appl. Environ. Microbiol. 37:938-942

From the foregoing example, it is apparent that the purified cellobiase enzyme prepared in accordance with this invention is very effective for the conversion of cellobiose to glucose.

As an alternative embodiment of the present invention, enzymes extracted from *Trichoderma reesei* and from *Aspergillus terreus* may be combined for the conversion of cellulose to glucose in a single fermentation step.

It will be understood by those skilled in the art that the conversion of cellulose to cellobiose may be carried out by using enzymes from the cultures rather than the cultures per se. The cells may be separated from the culture medium or broth and the broth which contains enzymes used in the treatment of cellulosic feedstock.

Alternatively, the techinque disclosed herein for the preparation of the cellobiase enzyme may be employed for the preparation of the cellulase enzyme.

We claim:

1. A method for converting cellobiose to glucose which comprises contacting cellobiose with a purified cellobiase enzyme prepared by extracting a biomass of a cellobiase-producing mold with an aqueous buffer thereby producing a crude enzyme extract, contacting said crude enzyme extract at a pH of 6 with anion and cation exchange resins effecting removal of a major portion of the contaminating protein associated therewith, and contacting the purified cellobiase enzyme with cellobiose under cellobiose conversion conditions.

2. A method according to claim 1 wherein said cellobiase enzyme is extracted from *Aspergillus terreus*.

3. A method according to claim 2 wherein said anion exchange resin contains diethylaminoethyl groups and said cation exchange resin contains carboxymethyl groups.

4. A method according to claim 1 wherein said aqueous buffer comprises a 0.05 molar aqueous solution of potassium phosphate.

5. A method according to claim 1 wherein said cellobiose is derived from a cellulosic feedstock by the action of *Trichoderma reesei*.

6. A method for purifying an aqueous cellobiase enzyme extract prepared from a cellobiase-producing mold which comprises contacting said extract at a pH of 6 with anion and cation exchange resins thereby effecting removal of a major portion of the contaminating protein associated with said enzyme.

7. A method according to claim 6 wherein said anion exchange resin comprises diethylaminoethyl groups and said cation exchange resin comprises carboxymethyl groups.

8. A method according to claim 6 wherein said cellobiase enzyme is extracted from *Aspergillus terreus* cells.

9. A process for converting cellulose to glucose comprising, contacting a cellulosic feedstock with a biomass containing *Trichoderma reesei* in an aqueous medium under cellulose conversion conditions to produce cellobiose, separating the aqueous solution containing cellobiose from said biomass, and contacting under cellobiose conversion conditions said aqueous solution containing the cellobiose with a purified cellobiase anzyme prepared by extracting a biomass of a cellobiase-producing mold with an aqueous buffer to produce a crude enzyme extract and contacting said crude enzyme extract at a pH of 6 with anion and cation exchange resins thereby effecting removal of a major portion of the contaminating protein associated with said enzyme.

10. An enzyme composition for converting cellulose to glucose comprising purified cellobiase enzyme extracted from *Aspergillus terreus* characterized as having a Ki dissociation constant of $3.5 \times 10^{-3}$M for glucose and a Km affinity of $4.0 \times 10^{-4}$M for cellulose and cellulase enzymes extracted from *Trichoderma reesei*.

11. An immobilized enzyme composition for the conversion of cellulose to glucose, comprising the composition of claim 10 and a suitable carrier material.

12. A method for converting cellulose to glucose comprising contacting cellulose with the composition of claim 10.

13. A method according to claim 6 wherein said purified cellobiase enzyme is immobilized on a carrier material.

14. A process of converting cellobiose to glucose employing the method of claim 6.

15. The process of claim 9 wherein the cellobiase enzyme is extracted from *Aspergillus terreus*.

16. A purified enzyme comprising cellobiase extracted from *Aspergillus terreus* characterized as having a Ki dissociation constant of $3.5 \times 10^{-3}$M for glucose and a Km affinity of $4 \times 10^{-4}$M for cellulose.

17. The enzyme of claim 16 wherein said enzyme is immobilized on a carrier material.

18. A method of converting cellobiose to glucose comprising contacting cellobiose with a purified cellobiase enzyme extracted from *Aspergillus terreus* characterized as having a Ki dissociation constant of $3.5 \times 10^{-3}$M for glucose and a Km affinity of $4.0 \times 10^{-4}$M for cellobiose.

19. A method according to claim 18 wherein the purified cellobiase is immobilized as a carrier material.

* * * * *